United States Patent
Watanabe

(10) Patent No.: US 8,080,317 B2
(45) Date of Patent: Dec. 20, 2011

(54) GRANULE COATED WITH URETHANE RESIN

(75) Inventor: Atsushi Watanabe, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 191 days.

(21) Appl. No.: 12/600,506

(22) PCT Filed: Jun. 28, 2007

(86) PCT No.: PCT/JP2007/063412
§ 371 (c)(1), (2), (4) Date: Nov. 17, 2009

(87) PCT Pub. No.: WO2009/001477
PCT Pub. Date: Dec. 31, 2008

(65) Prior Publication Data
US 2010/0151250 A1  Jun. 17, 2010

(51) Int. Cl.
*B32B 5/16* (2006.01)

(52) U.S. Cl. ............... 428/407; 528/64; 528/66; 528/86

(58) Field of Classification Search .................. 428/403, 428/407; 528/64, 66, 86
See application file for complete search history.

(56) References Cited

U.S. PATENT DOCUMENTS

| | | | | |
|---|---|---|---|---|
| 5,496,496 A | * | 3/1996 | Kajita et al. | 252/182.24 |
| 6,023,547 A | * | 2/2000 | Tortorello | 385/114 |
| 6,176,891 B1 | | 1/2001 | Komoriya et al. | |
| 6,364,925 B1 | | 4/2002 | Markusch et al. | |
| 7,220,469 B2 | * | 5/2007 | Sakane et al. | 428/32.66 |
| 2003/0125499 A1 | * | 7/2003 | Benz et al. | 528/44 |
| 2005/0031871 A1 | * | 2/2005 | Kinsho et al. | 428/402 |
| 2010/0189799 A1 | * | 7/2010 | Watanabe | 424/497 |

FOREIGN PATENT DOCUMENTS

| | | |
|---|---|---|
| EP | 0867422 A2 | 9/1998 |
| EP | 1106635 A2 | 6/2001 |
| JP | 10029886 A | 2/1998 |
| JP | 11005704 A | 1/1999 |
| JP | 2916762 B2 | 4/1999 |
| JP | 2003183104 A | 7/2003 |
| JP | 2004203667 A | 7/2004 |
| JP | 2007210960 A | 8/2007 |

* cited by examiner

*Primary Examiner* — Hoa (Holly) Le
(74) *Attorney, Agent, or Firm* — Panitch Schwarze Belisario & Nadel LLP

(57) ABSTRACT

A coated granule obtained by coating a bioactive substance-containing granule with a urethane resin obtained by reaction of an aromatic polyisocyanate with a polyol having an average molecular weight of 300 to 5000, wherein the polyol contains a polycaprolactonepolyol and a hydroxy fatty acid ester of the formula (I): (wherein, X represents —CH2-CH2- or —CH=CH—, n represents 1, 2 or 3, m represents 0, 1 or 2, and n+m is 2 or 3. In the case of n+m=2, A represents a C2 to C8 alkanediyl group, and in the case of n+m=3, A represents a C3 to C8 alkanetriyl group.) as the coat film, is capable of controlling elution of the bioactive substance appropriately, and, the urethane resin forming the coat film shows degradability in soil.

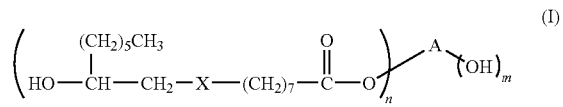

12 Claims, No Drawings

GRANULE COATED WITH URETHANE RESIN

CROSS-REFERENCE TO RELATED APPLICATION

This application is a section 371 of International Application No. PCT/JP2007/063412, filed Jun. 28, 2007, which was published in the English language on Dec. 31, 2008 under International Publication No. WO 2009/001477 A1 and the disclosure of which is incorporated herein by reference.

TECHNICAL FIELD

The present invention relates to a granule coated with a urethane resin.

BACKGROUND TECHNOLOGY

There is suggested a technology of coating a bioactive ingredient for fertilizers, pesticides and the like with a coat film, thereby controlling elution appropriately, so as to cause elution thereof at given period according to the growth of plants (see, e.g., JP10-029886A, JP11-005704A).

Recently, enhanced attention is paid to easily degradable resins for thoughtful consideration for the environment. With coated granules of a bioactive substance, however, it is difficult to control elution using an easily degradable resin as a coat film so as to elute a bioactive component at given period.

DISCLOSURE OF THE INVENTION

According to the present invention, with a coated granule of a bioactive substance, use of a urethane resin obtained by reacting an aromatic polyisocyanate with a polyol having an average molecular weight of 300 to 5000 in which the polyol contains a polycaprolactonepolyol and a hydroxy fatty acid ester of the formula (I):

$$\left( HO-\underset{|}{\underset{(CH_2)_5CH_3}{CH}}-CH_2-X-(CH_2)_7-\overset{O}{\overset{\|}{C}}-O \right)_n A\text{-}(OH)_m \quad (I)$$

(wherein, X represents —$CH_2$—$CH_2$— or —CH=CH—, n represents 1, 2 or 3, m represents 0, 1 or 2, and n+m is 2 or 3. In the case of n+m=2, A represents a $C_2$ to $C_8$ alkanediyl group, and in the case of n+m=3, A represents a $C_3$ to $C_8$ alkanetriyl group.), as the coat film, is capable of controlling elution of the bioactive substance appropriately, and, the urethane resin forming the coat film shows degradability in soil.

That is, the present invention includes the following invention.

[Invention 1]

A coated granule obtained by coating a bioactive substance-containing granule with a urethane resin obtained by reaction of an aromatic polyisocyanate with a polyol having an average molecular weight of 300 to 5000, wherein the polyol contains a polycaprolactonepolyol and a hydroxy fatty acid ester of the formula (I):

$$\left( HO-\underset{|}{\underset{(CH_2)_5CH_3}{CH}}-CH_2-X-(CH_2)_7-\overset{O}{\overset{\|}{C}}-O \right)_n A\text{-}(OH)_m \quad (I)$$

(wherein, X represents —$CH_2$—$CH_2$— or —CH=CH—, n represents 1, 2 or 3, m represents 0, 1 or 2, and n+m is 2 or 3. In the case of n+m=2, A represents a $C_2$ to $C_8$ alkanediyl group, and in the case of n+m=3, A represents a $C_3$ to $C_8$ alkanetriyl group.).

[Invention 2]

The coated granule according to Invention 1, wherein the total content of a polycaprolactonepolyol and a hydroxy fatty acid ester of the formula (I) in the polyol is 50 wt % or more.

[Invention 3]

The coated granule according to Invention 1, which is obtained by coating a bioactive substance-containing granule with a urethane resin obtained by reaction of an aromatic polyisocyanate with a polyol having an average molecular weight of 300 to 5000, wherein the polyol contains a polycaprolactonepolyol and at least one selected from castor oil and hydrogenated castor oil.

[Invention 4]

The coated granule according to Invention 3, wherein the total content of a polycaprolactonepolyol and at least one selected from castor oil and hydrogenated castor oil in the polyol is 70 wt % or more.

[Invention 5]

The coated granule according to any one of Inventions 1 to 4, wherein the amount of the polycaprolactonepolyol is 20 to 80 parts by weight based on 100 parts by weight of the total amount of the aromatic polyisocyanate and polyol.

[Invention 6]

The coated granule according to any one of Inventions 1 to 5, wherein the amount of the hydroxy fatty acid ester of the formula (I) is 10 to 60 parts by weight based on 100 parts by weight of the total amount of the aromatic polyisocyanate and polyol.

[Invention 7]

The coated granule according to any one of Inventions 1 to 6, wherein the amount of the aromatic polyisocyanate is 15 to 60 parts by weight based on 100 parts by weight of the total amount of the aromatic polyisocyanate and polyol.

[Invention 8]

The coated granule according to any one of Inventions 1 and 4 to 7, wherein the total amount of the aromatic polyisocyanate, polycaprolactonepolyol and hydroxy fatty acid ester of the formula (I) is 70 to 100 parts by weight based on 100 parts by weight of the total amount of the aromatic polyisocyanate and polyol.

[Invention 9]

The coated granule according to any one of Inventions 1 and 4 to 8, wherein the hydroxy fatty acid ester of the formula (I) is triglyceride ricinoleate.

[Invention 10]

The coated granule according to any one of Inventions 1 to 9, wherein the aromatic polyisocyanate is polymethylenepolyphenyl polyisocyanate.

[Invention 11]

The coated granule according to any one of Inventions 1 to 10, wherein the bioactive substance is a fertilizer.

[Invention 12]

The coated granule according to any one of Inventions 1 to 10, wherein the bioactive substance is a pesticide.

DETAILED DESCRIPTION OF THE INVENTION

According to the present invention, the coated granule containing a bioactive substance is coated with a resin easily degradable in soil and shows excellent elution controllability of the bioactive substance.

The urethane resin used as a coat film of the coated granular material of the present invention is a urethane resin obtained by reaction of an aromatic polyisocyanate with a polyol having an average molecular weight of 300 to 5000 containing a polycaprolactonepolyol and a hydroxy fatty acid ester of the formula (I). The content of a polycaprolactonepolyol and a hydroxy fatty acid ester of the formula (I) in the polyol is usually 50 wt % or more. Instead of the hydroxy fatty acid ester of the formula (I), castor oil or hydrogenated castor oil as a vegetable oil containing a hydroxy fatty acid ester of the formula (I) can also be used. In this case, the total content of a polycaprolactonepolyol and at least one selected from castor oil and hydrogenated castor oil in the polyol is usually 70 wt % or more. Here, the polyol having a molecular weight of 300 to 5000 means that the number average molecular weight of a polycaprolactonepolyol, a hydroxy fatty acid ester of the formula (I), and other polyols contained if necessary, as a whole, is in the range of 300 to 5000. The number average molecular weight is measured by a quantitative analysis for terminal group.

The polycaprolactonepolyol is a compound produced by ring-opening-polymerizing an ε-caprolactone monomer with a low molecular weight polyol. The low molecular weight polyol is a compound of 2 to 8 carbon atoms having two or more hydroxyl groups in one molecule, and examples of polyols having two hydroxyl groups in one molecule include ethylene glycol, diethylene glycol, propylene glycol, 1,4-butanediol, 1,5-pentanediol, 1,6-hexanediol and 1,8-octanediol, and examples of polyols having three hydroxyl groups in one molecule include 2-ethyl-2-(hydroxymethyl)-1,3-propanediol (trimethylolpropane), 2-(hydroxymethyl)-1,3-propanediol, glycerin and triethanolamine. Typical chemical structures of the polycaprolactonepolyol (polycaprolactonediol or polycaprolactonetriol) having two or three hydroxyl groups in one molecule are shown below. This polycaprolactonepolyol is a polyol having at least one (1-oxohexa-1,6-diyl)oxy structure ($-C(=O)-CH_2-CH_2-CH_2-CH_2-CH_2-O-$) in one molecule.

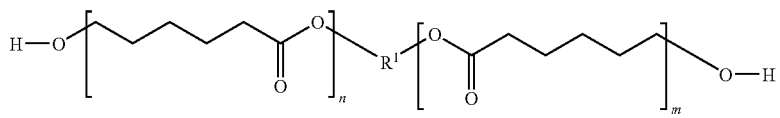

[wherein, m represents an integer of 0 or more, n represents an integer of 1 or more and m+n is 2 or more, and $R^1$ represents a divalent organic group (for example, ethylene group, tetramethylene group and the like)].

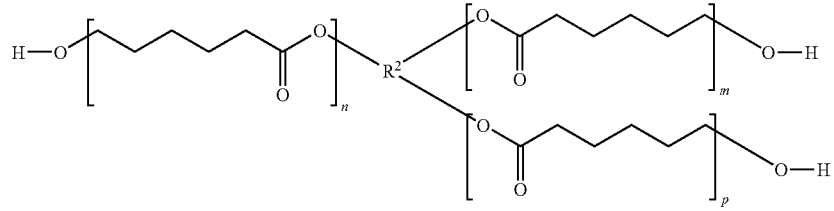

[wherein, m and p represent an integer of 0 or more, n represents an integer of 1 or more and m+n+p is 2 or more, and $R^2$ represents a trivalent organic group (for example, propane-1,2,3-triyl group and the like)].

In the present invention, the amount of the aromatic polyisocyanate is preferably 15 to 60 parts by weight, more preferably 20 to 50 parts by weight based on 100 parts by weight of the total amount of the aromatic polyisocyanate and the polyol.

Examples of the aromatic polyisocyanate include 4,4'-diphenylmethane diisocyanate (MDI), tolylene diisocyanate (TDI), xylylene diisocyanate (XDI), tolidine diisocyanate (TODI), naphthalene 1,5-diisocyanate (NDI), tetramethylenexylylene diisocyanate (TMXDI), polymethylenepolyphenyl polyisocyanate (polymeric MDI) or derivatives thereof (modified substances such as isocyanurate, biuret, urethodione and the like). Particularly, aromatic polyisocyanates in which one isocyanate group is directly connected to one benzene ring are preferable, and specific examples of such aromatic polyisocyanates include MDI, TODI and polymeric MDI, and most preferable is polymeric MDI.

In the present invention, the proportion of a polycaprolactonepolyol is preferably 20 to 80 parts by weight based on 100 parts by weight of the total amount of the aromatic polyisocyanate and the polyol.

In the present invention, polycaprolactonepolyols having a molecular weight of 400 to 2500 are preferable. The hydroxyl equivalent of a polycaprolactonepolyol is preferably 200 to 1250. Here, the hydroxyl equivalent means the molecular weight of a polyol per hydroxyl group. The hydroxyl equivalent of a polyol is measured by a quantitative analysis for terminal group.

In the present invention, the proportion of a hydroxy fatty acid ester of the formula (I) is preferably 10 to 60 parts by weight, more preferably 14 to 50 parts by weight based on 100 parts by weight of the total amount of an aromatic polyisocyanate and a polyol.

The hydroxy fatty acid ester of the formula (I) is produced by dehydration-condensing ricinoleic acid or 12-hydroxystearic acid with the above-mentioned low molecular weight polyol, and ricinoleic acid or 12-hydroxystearic acid is condensed in a proportion of 1 to 3 molecules with one molecule of a low molecular weight polyol.

In production of a hydroxy fatty acid ester of the formula (I), regarding the low molecular weight polyol to be used as a raw material, examples of compounds having two hydroxyl groups in one molecule include ethylene glycol, diethylene glycol, propylene glycol, 1,4-butanediol, 1,5-pentanediol, 1,6-hexanediol and 1,8-octanediol, and examples of polyols having three hydroxyl groups in one molecule include 2-ethyl-2-(hydroxymethyl)-1,3-propanediol (trimethylolpropane), 2-(hydroxymethyl)-1,3-propanediol and 1,2,3-propanetriol (glycerin).

In the formula (I), when the low molecular weight polyol to be used as a raw material has two hydroxyl groups in one molecule, n+m is 2, n is 1 or 2, and A is a $C_2$ to $C_8$ alkanediyl group (for example, ethane-1,2-diyl group, propane-1,3-diyl group, butane-1,4-diyl group, pentane-1,5-diyl group, hexane-1,6-diyl group), and when the low molecular weight polyol has three hydroxyl groups in one molecule, n+m is 3, n is 1, 2 or 3, and A is a $C_3$ to $C_8$ alkanetriyl group (for example, propane-1,2,3-triyl group).

In the hydroxy fatty acid ester of the formula (I), triglyceride ricinoleate is a main component contained in a proportion of about 70 wt % in castor oil, and as the triglyceride ricinoleate, castor oil and hydrogenated castor oil (hardened castor oil) can be used. Further, ricinoleic acid obtained by hydrolysis of castor oil can also be used for producing a hydroxy fatty acid ester of the formula (I). 12-Hydroxystearic acid can be obtained by hydrogenation of ricinoleic acid.

As the hydroxy fatty acid ester of the formula (I), triglyceride ricinoleate is preferably used. It is also convenient to use castor oil or hydrogenated castor oil as the hydroxy fatty acid ester of the formula (I).

In the present invention, the molar ratio of a polycaprolactonepolyol to a hydroxy fatty acid ester of the formula (I) to be used is not particularly restricted, and preferably in the range of 1:0.1 to 1:5.

In the present invention, the polyol for obtaining a urethane resin may be a mixture composed only of a polycaprolactonepolyol and a hydroxy fatty acid ester of the formula (I), or a mixture composed of a polycaprolactonepolyol and castor oil or hydrogenated castor oil. Further, other polyols may also be contained.

Examples of the other polyols include polyether polyols such as polyoxypropylenediol, polyoxypropylenetriol and the like.

In the present invention, the ratio of the mol number of an isocyanate group in an aromatic polyisocyanate to the mol number of a hydroxyl group in the polyol is preferably 1:0.9 to 1:1.5, more preferably 1:1 to 1:1.2.

The urethane resin is produced usually by reacting an aromatic polyisocyanate and a polyol, if necessary in the presence of a catalyst, on the surface of a bioactive substance-containing granule or on a coat film covering a bioactive substance-containing granule.

The reaction of an aromatic polyisocyanate and a polyol is not particularly restricted, and can be carried out by, for example, a method in which all aromatic polyisocyanates and polyols are mixed and hardened, a method in which aromatic polyisocyanates and a part of polyols are mixed previously to prepare a polyisocyanate-terminal prepolymer, then, remaining polyols are mixed and hardened, and other methods. Further, it is also possible that a small amount of organic solvent is mixed with a polyisocyanate and a polyol, and a solvent is removed simultaneously with the reaction. The reaction conditions thereof can be selected arbitrarily, however, when the temperature is raised, the reaction speed of a hydroxyl group and an isocyanate group increases. By adding a catalyst, the reaction speed can be accelerated.

Examples of the catalyst to be used for production of a urethane resin include organometal compounds such as potassium acetate, calcium acetate, stannous octoate, dibutyltin diacetate, dibutyltin dichloride, dibutyltin dilaurate, dibutinthiostannic acid, stannous octylate, di-n-octyltin dilaurate, isopropyl titanate, bismuth 2-ethyl hexanoate, phosphine, zinc neodecanoate, tetrabutyl titanate, oxyisopropyl vanadate, n-propyl zirconate and the like, and amine catalysts such as triethylamine, N,N,N',N'-tetramethylethylenediamine, triethylenediamine, N-methylmorpholine, N,N-dimethyldidodecylamine, N-dodecylmorpholine, N,N-dimethylcyclohexylamine, N-ethylmorpholine, dimethylethanolamine, N,N-dimethylbenzylamine, 2,4,6-tris(dimethylaminomethyl)phenol and the like.

A mixture having flowability of an aromatic polyisocyanate and a polyol (further, catalyst to be added if necessary), before sufficient reaction of a diisocyanate group in the aromatic polyisocyanate and a hydroxyl group in the polyol, is expressed as an unhardened urethane resin in some cases.

The coated granule of the present invention is a coated granule obtained by coating a bioactive substance-containing granule with a urethane resin, and the coat using a urethane resin suppresses elution of a bioactive substance in the bioactive substance-containing granule. In the present invention, mentioned as the bioactive substance contained in the bioactive substance-containing granule are insecticides, fungicides, herbicides, plant growth regulating agents, repellents, fertilizers and the like.

Examples of the pesticidal ingredient for insecticides, fungicides, herbicides, plant growth regulating agents, repellents and the like include organophosphorus compounds such as fenitrothion [O,O-dimethyl O-(3-methyl-4-nitrophenyl) phosphorothioate], fenthion [O,O-dimethyl O-(3-methyl-4-(methylyhio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidothioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorodithioate], DDVP [2,2-dichlorovinyl dimethylphosphate], sulprofos [O-ethyl O-4-(methylyhio)phenyl S-propylphosphorodithioate], cyanophos [O-4-cyanophenyl O-dimethyl phosphorothioate], dioxabenzofos [2-methoxy-4H-1,3,2-benzodioxaphosphorine-2-sulfide], dimethoate [O,O-dimethyl S—(N-methylcarbamoylmethyl) dithiophosphate], phenthoate [ethyl 2-dimethoxyphosphinothioyl(phenyl)acetate], malathion [diethyl (dimethoxyphosphinothioylthio)succinate], trichlorfon [dimethyl 2,2,2-trichloro-1-hydroxyethylphosphonate], azinphos-methyl [S-3,4-dihydro-4-oxo-1,2,3-benzotriazin-3-ylmethyl O,O-dimethyl phosphorodithioate], monocrotophos [dimethyl (E)-1-methyl-2-(methylcarbamoyl)vinyl phosphate] and ethion [O, O, O', O'-tetraethyl S,S'-methylenebis (phosphorodithioate)]; carbamate compounds such as BPMC [2-sec-butylphenyl methylcarbamate], benfuracarb [ethyl N-{2,3-dihydro-2,2-dimethylbenzofuran-7-yloxycarbonyl(methyl) aminothio}-N-isopropyl-β-alaninate], propoxur [2-isopropoxyphenyl N-methylcarbamate], carbosulfan[2,3-dihydro-2,2-dimethyl-7-benzo[b]furanyl N-dibutylaminothio-N-methylcarbamate], carbaryl [1-naphthyl N-methylcarbamate], methomyl [S-methyl-N-(methylcarbamoyloxy) thioacetimidate], ethiofencarb [2-(ethylthiomethyl)phenyl methylcarbamate], aldicarb [2-methyl-2-(methylthio) propionaldehyde O-methylcarbamoyl oxime], oxamyl [N,N-dimethyl-2-methylcarbamoyloxyimino-2-(methylthio)acetamide] and fenothiocarb [S-4-phenoxybutyl N,N-dimethylthiocarbamate]; pyrethroid compounds such as etofenprox [2-(4-ethoxyphenyl)-2-methyl-1-(3-phenoxybenzyl)oxypropane], fenvalerate [(RS)-α-cyano-(3-phenoxybenzyl) (RS)-2-(4-chlorophenyl)-3-methylbutyrate], esfenvalerate [(S)-α-cyano-(3-phenoxybenzyl) (S)-2-(4-chlorophenyl)-3-methylbutyrate], fenpropathrin [(RS)-α-cyano-(3-phenoxybenzyl) 2,2,3,3-tetramethylcyclopropanecarboxylate], cypermethrin [(RS)—α-cyano-(3-phenoxybenzyl) (1RS)-cis,trans-3-(2,2-dichlorovinyl)-2,2-dimethylcyclopropanecarboxylate], permethrin [3-phenoxybenzyl (1RS)-cis,trans-3-(2,2-dichlorovinyl)-2,2-dimethylcyclopropanecarboxylate], cyhalothrin [(RS)-α-cyano-(3-phenoxybenzyl) (1RS,3Z)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichlorovinyl-1-(4-ethoxyphenyl)cyclopropanecarboxylate], fluvalinate [α-cyano-3-phenoxybenzyl N-(2-chloro-α,α,α-trifluoro-p-tolyl)-D-valinate], biphenthrin [2-methyl-3-phenylbenzyl (1RS,3Z)-cis-3-(2-chloro-3,3,3-trifluoro-1-propenyl)-2,2-dimethylcyclopropanecarboxylate], halfenprox [2-(4-bromodifluoromethoxyphenyl)-2-methyl-1-(3-phenoxybenzyl)methylpropane], tralomethrin [(S)-α-cyano-3-phenoxybenzyl (1R)-cis-3-(1,2,2,2-tetrabromoethyl)-2,2-dimethylcyclopropanecarboxylate], silafluofen [(4-ethoxyphenyl)-{3-(4-fluoro-3-phenoxyphenyl) propyl}dimethylsilane], d-phenothrin [3-phenoxybenzyl (1R)-cis,trans-2,2-dimethyl-3-(2-methyl-1-propenyl) cyclopropanecarboxylate], cyphenothrin [(RS)-α-cyano-3-phenoxybenzyl (1R)-cis,trans-2,2-dimethyl-3-(2-methyl-1-propenyl)cyclopropanecarboxylate], d-resmethrin [5-benzyl-3-furylmethyl (1R)-cis,trans-2,2-dimethyl-3-(2-methyl-1-propenyl) cyclopropanecarboxylate], acrinathrin [(S)-α-cyano-3-phenoxybenzyl (1R,3Z)-cis-2,2-dimethyl-3-{3-oxo-(1,1,1,3,3,3-hexafluoropropyloxy) propenyl}cyclopropanecarboxylate), cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS,3Z)-cis-3-(2-chloro-3,3,3-trifluoro-1-propenyl)-2,2-dimethylcyclopropanecarboxylate], transfluthrin [2,3,5,6-tetrafluorobenzyl (1R)-trans-3-(2,2-dichlorovinyl)-2,2-dimethylcyclopropanecarboxylate], tetramethrin [3,4,5,6-tetrahydrophthalimidomethyl (1RS)—cis,trans-2,2-dimethyl-3-(2-methyl-1-propenyl) cyclopropanecarboxylate], allethrin [(RS)-2-methyl-4-oxo-3-(2-propenyl)-2-cyclopenten-1-yl (1RS)-cis,trans-2,2-dimethyl-3-(2-methyl-1-propenyl)cyclopropanecarboxylate], prallethrin [(S)-2-methyl-4-oxo-3-(2-propynyl)-2-cyclopenten-1-yl (1R)-cis,trans-2,2-dimethyl-3-(2-methyl-1-propenyl)cyclopropanecarboxylate], empenthrin [(RS)-1-ethynyl-2-methyl-2-pentenyl (1R)-cis,trans-2,2-dimethyl-3-(2-methyl-1-propenyl)cyclopropanecarboxylate], imiprothrin [2,5-dioxo-3-(2-propynyl)imidazolidin-1-ylmethyl (1R)-cis,trans-2,2-dimethyl-3-(2-methyl-1-propenyl) cyclopropanecarboxylate], d-furamethrin [5-(2-propynyl) furfuryl (1R)-cis,trans-2,2-dimethyl-3-(2-methyl-1-propenyl) cyclopropanecarboxylate] and 5-(2-propynyl)furfuryl 2,2,3,3-tetramethylcyclopropanecarboxylate; thiadiazine derivatives such as buprofezin [2-tert-butylimino-3-isopropyl-5-phenyl-1,3,5-thiadiazin-4-one]; nitroimidazolidine derivatives; nereistoxin derivatives such as cartap [S,S'-(2-dimethylaminotrimethyl)bis(thiocarbamate)], thiocyclam [N,N-dimethyl-1,2,3-trithian-5-yl-amine] and bensultap [S,S'-2-dimethylaminotrimethylenedi (benzenethiosulfonate); N-cyanoamidine derivatives such as N-cyano-N'-methyl-N'-(6-chloro-3-pyridylmethyl)acetamide; chlorinated hydrocarbon compounds such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and dicofol[1,1-bis(4-chlorophenyl)-2,2,2-trichloroethanol]; benzoylphenylurea compounds such as chlorfluazuron [1-{3,5-dichloro-4-(3-chloro-5-trifluoromethylpyridin-2-yloxy) phenyl}-3-(2,6-difluorobenzoyl)urea], teflubenzuron [1-(3,5-dichloro-2,4-difluorophenyl)-3-(2,6-difluorobenzoyl)urea] and flufenoxuron [1-{4-(2-chloro-4-trifluoromethylphenoxy)-2-fluorophenyl}-3-(2,6-difluorobenzoyl)urea]; formamidine derivatives such as amitraz [N,N-{(methylimino)dimethylidine}-di-2,4-xyiidine] and chlorodimeform [N'-(4-chloro-2-methylphenyl)-N,N-dimethylmethinimidamide]; thiourea derivatives such as diafenthiuron [N-(2,6-diisopropyl-4-phenoxyphenyl)-N'-t-butylcarbodiimide]; N-phenylpyrazole compounds; metoxadiazon [5-methoxy-3-(2-methoxyphenyl)-1,3,4-oxadiazol-2(3H)-one]; bromopropylate [isopropyl 4,4'-dibromobenzilate]; tetradifon [4-chlorophenyl 2,4,5-trichlorophenyl sulfone]; chinomethionat [S,S-6-methylquinoxaline-2,3-diyldithiocarbonate]; propargite [2-(4-tert-butylphenoxy)cyclohexylprop-2-yl sulfite]; fenbutatin oxide [bis(tris(2-methyl-2-phenylpropyl)tin)oxide]; hexythiazox [(4RS,5RS)-5-(4-chlorophenyl)-N-chlorohexyl-4-methyl-2-oxo-1,3-thiazolidine-3-carboxamide]; clofentezine[3,6-bis(2-chlorophenyl)-1,2,4,5-tetrazine]; pyridaben [2-tert-butyl-5-(4-tert-butylbenzylthio)-4-chloropyridazin-3(2H)-one]; fenpyroximate [tert-butyl (E)-4-[(1,3-dimethyl-5-phenoxypyrazol-4-yl)methyleneaminooxymethyl]benzoate]; tebufenpyrad [N-4-tert-butylbenzyl]-4-chloro-3-ethyl-1-methyl-5-pyrazolcarboxamide]; polynactin complex [tetranactin, dinactin, trinactin]; pyrimidifen [5-chloro-N-[2-{4-(2-ethoxyethyl)-2,3-dimethylphenoxy}ethyl]-6-ethylpyrimidine-4-amine]; milbemectin; abamectin, ivermectin; azadirachtin [AZAD]; 5-methyl[1,2,4]triazolo[3,4-b]benzothiazol; methyl 1-(butylcarbamoyl)benzimidazol-2-carbamate; 6-(3,5-dichloro-4-methylphenyl)-3(2H)-pyridazinone; 1-(4-chlorophenoxy)-3,3-dimethyl-1-(1H-1,2,4-triazol-1-yl)butanone; (E)-4-chloro-2-(trifluoromethyl)-N-[1-(imidazol-1-yl)-2-propoxyethylidene] aniline; 1-[N-propyl-N-[2-(2,4,6-trichlorophenoxy)ethyl] carbamoyl]imidazole; (E)-1-(4-chlorophenyl)-4,4-dimethyl-2-(1H-1,2,4-triazol-1-yl)-1-penten-3-ol; 1-(4-chlorophenyl)-4,4-dimethyl-2-(1H-1,2,4-triazol-1-yl)pentan-3-ol; (E)-1-(2,4-dichlorophenyl)-4,4-dimethyl-2-(1H-1,2,4-triazol-1-yl) penten-3-ol; 1-(2,4-dichlorophenyl)-4,4-dimethyl-2-(1H-1,2,4-triazol-1-yl) pentan-3-ol; 4-[3-(4-tert-butylphenyl)-2-methylpropyl]-2,6-dimethylmorpholine; 2-(2,4-dichlorophenyl)-1-(1H-1,2,4-triazol-1-yl)hexan-2-ol; O,O-diethyl O-2-quinoxalinyl phosphorothioate; 0-(6-ethoxy-2-ethyl-4-pyromidinyl) O,O-dimethyl phosphorothioate; 2-diethylamino-5,6-dimethylpyrimidin-4-yl dimethylcarbamate; 4-(2,4-dichlorobenzoyl)-1,3-dimethyl-5-pyrazolyl p-toluenesulfonate; 4-amino-6-(1,1-dimethylethyl)-3-methylthio-1,2,4-triazin-5(4H)-one; 2-chloro-N-[(4-methoxy-6-methyl-1,3,5-triazin-2-yl)aminocarbonyl] benzenesulfonamide; 2-methoxycarbonyl-N-[(4,6-dimethoxypyrimidin-2-yl)aminocarbonyl]benzenesulfonamide; 2-methoxycarbonyl-N-[(4,6-dimethylpyrimidin-2-yl) aminocarbonyl] benzenesulfonamide; 2-methoxycarbonyl-N-[(4-methoxy-6-methyl-1,3,5-triazin-2-yl)aminocarbonyl] benzenesulfonamide; 2-ethoxycarbonyl-N-[(4-chloro-6- methoxypyrimidin-2-yl)aminocarbonyl]benzenesulfonamide; 2-(2-chloroethoxy)-N-[(4-methoxy-6-methyl-1,3,5-triazin-2-yl) aminocarbonyl]benzenesulfonamide; 2-methoxycarbonyl-N-[(4,6-dimethoxypyrimidin-2-yl)aminocarbonyl] phenylmethanesulfonamide; 2-methoxycarbonyl-N-[(4-methoxy-6-methyl-1,3,5-triazin-2-yl)aminocarbonyl]thiophene-3-sulfonamide; 4-ethoxycarbonyl-N-[(4,6-dimethoxypyrimidin-2-yl)aminocarbonyl]-1-methylpyrazole-5-sulfonamide; 2-[4,5-dihydro-4-methyl-4-(1-methylethyl)-5-oxo-1H-imidazol-2-yl]-3-quinolinecarboxylic acid; 2-[4,5-dihydro-4-methyl-4-(1-methylethyl)-5-oxo-1H-imidazol-2-yl]-5-ethyl-3-pyridinecarboxylic acid; methyl 6-(4-isopropyl-4-methyl-5-oxoimidazolin-2-yl)-m-toluate; methyl 2-(4-isopropyl-4-methyl-5-oxoimidazolin-2-yl)-p-toluate; 2-(4-isopropyl-4-methyl-5-oxoimidazolin-2-yl)nicotinic acid; N-(4-chlorophenyl)methyl-N-cyclopentyl-N'-phenylurea; (RS)-2-cyano-N-[(R)-1-(2,4-dichlorophenyl)ethyl]-3,3-dimethylbutyramide; N-(1,3-dihydro-1,1,3-trimethylisobenzofuran-4-yl)-5-chloro-1,3-dimethylpyrazole-4-carboxamide; N-[2,6-dibrobo-4-(trifluoromethoxy)phenyl]-2-methyl-4-(trifluoromethyl)-5-thiazolecarboxamide; 2,2-dichloro-N-[1-(4-chlorophenyl)ethyl]-3-methylcyclopropanecarboxamide; methyl (E)-2-2-6-(2-cyanophenoxy)pyrimidin-4-yloxy-phenyl-3-methoxyacrylate; 5-methyl-1,2,4-triazolo[3,4-b]benzothiazole; 3-allyloxy-1,2-benzisothiazole-1,1-dioxide; diisopropyl 1,3-dithiolan-2-ylidenemalonate and O,O-dipropyl O-4-methylthio phosphate.

The fertilizer in the present invention is a component containing various elements such as nitrogen, phosphorus, potassium, silicon, magnesium, calcium, manganese, boron, iron and the like to be applied to soil for imparting nutrients in plant cultivation, and examples thereof include nitrogen fertilizer components such as urea, ammonium nitrate, magnesium ammonium nitrate, ammonium chloride, ammonium sulfate, ammonium phosphate, sodium nitrate, calcium nitrate, potassium nitrate, lime nitrogen, formaldehyde-condensed urea (UF), acetaldehyde-condensed urea (CDU), isobutylaldehyde-condensed urea (IBDU) and guanyl urea (GU); phosphoric acid fertilizer components such as calcium superphosphate, triple superphosphate of lime, fused phosphorus, humus phosphorus, calcined phosphorus, sintered phosphorus, magnesium superphosphate, ammonium polyphosphate, potassium metaphosphate, calcium metaphosphate, magnesium phosphate, ammonium sulfate phosphate, ammonium potassium phosphate nitrate, ammonium hydrochloride phosphate and the like; potassium fertilizer components such as potassium chloride, potassium sulfate, potassium sodium sulfate, potassium magnesia sulfate, potassium bicarbonate, potassium phosphate and the like; silic acid fertilizer components such as calcium silicate and the like; magnesia fertilizer components such as magnesium sulfate, magnesium chloride and the like; calcium fertilized components such as calcium oxide, calcium hydroxide, calcium carbonate and the like; manganese fertilizer components such as manganese sulfate, magnesia manganese sulfate, slag manganese and the like; boron fertilizer components such as boric acid, borate and the like; iron-containing fertilizer components such as steel slag and the like.

The bioactive substance-containing granule in the present invention may be a bioactive substance itself, or a material supporting a bioactive substance on a carrier. The bioactive substance-containing granule may contain various kinds of bioactive substances. The coated granule of the present invention may contain several bioactive substance-containing granules as an inner core simultaneously.

Examples of the carrier supporting a bioactive substance include kaolin minerals such as kaolinite and the like; mineral carriers such as montmorillonite, smectite, talc, agalmatolite, hydrous calcium silicate, calcium carbonate, zeolite, terra alba and the like; plant carriers such as cellulose, husk, starch, soybean powder and the like; water-soluble carries such as lactose, sucrose, dextrin, sodium chloride, sodium tripolyphosphate, and the like, and these carries can be used appropriately in combination.

In the present invention, mentioned as the bioactive substance-containing granule are pesticidal granules containing pesticidal active compounds such as insecticides, fungicides, herbicides, plant growth regulating agents, repellents and the like; granular fertilizers; pesticide-containing granular fertilizers containing fertilizers and pesticidal active ingredients, and the like.

As the coated granule of the present invention, the following embodiments are exemplified.

A coated granule obtained by coating a bioactive substance-containing granule with a urethane resin obtained by reacting 15 to 60 parts by weight of an aromatic polyisocyanate with a polyol containing 20 to 80 parts by weight of a polycaprolactonepolyol and 10 to 60 parts by weight of a hydroxy fatty acid ester of the formula (I).

A coated granule obtained by coating a bioactive substance-containing granule with a urethane resin obtained by reacting 20 to 50 parts by weight of an aromatic polyisocyanate with a polyol containing 20 to 80 parts by weight of a polycaprolactonepolyol and 14 to 50 parts by weight of a hydroxy fatty acid ester of the formula (I).

A coated granule obtained by coating a bioactive substance-containing granule with a urethane resin obtained by reacting 15 to 60 parts by weight of an aromatic polyisocyanate with a polyol containing 20 to 80 parts by weight of a polycaprolactonepolyol and 10 to 60 parts by weight of triglyceride ricinoleate.

A coated granular material obtained by coating a bioactive substance-containing granule with a urethane resin obtained by reacting 20 to 50 parts by weight of an aromatic polyisocyanate with a polyol containing 20 to 80 parts by weight of a polycaprolactonepolyol and 14 to 50 parts by weight of triglyceride ricinoleate.

A coated granular material obtained by coating a bioactive substance-containing granule with a urethane resin obtained by reacting 15 to 60 parts by weight of an aromatic polyisocyanate with a polyol containing 20 to 80 parts by weight of a polycaprolactonepolyol and 10 to 60 parts by weight of triglyceride ricinoleate.

A coated granular material obtained by coating a bioactive substance-containing granule with a urethane resin obtained by reacting 20 to 50 parts by weight of an aromatic polyisocyanate with a polyol containing 20 to 80 parts by weight of a polycaprolactonepolyol and 14 to 50 parts by weight of triglyceride ricinoleate.

A coated granular material obtained by coating a bioactive substance-containing granule with a urethane resin obtained by reacting 15 to 60 parts by weight of an aromatic polyisocyanate with a polyol containing 20 to 80 parts by weight of a polycaprolactonepolyol and 10 to 60 parts by weight of a hydroxy fatty acid ester of the formula (I), the ratio of the molar quantity of an isocyanate group in the aromatic polyisocyanate to the molar quantity of a hydroxyl group in the polyol being 1:1 to 1:1.2.

A coated granule obtained by coating a bioactive substance-containing granule with a urethane resin obtained by reacting 20 to 50 parts by weight of an aromatic polyisocyanate with a polyol containing 20 to 80 parts by weight of a polycaprolactonepolyol and 14 to 50 parts by weight of a hydroxy fatty acid ester of the formula (I), the ratio of the molar quantity of an isocyanate group in the aromatic polyisocyanate to the molar quantity of a hydroxyl group in the polyol being 1:1 to 1:1.2.

A coated granule obtained by coating a bioactive substance-containing granule with a urethane resin obtained by reacting 15 to 60 parts by weight of an aromatic polyisocyanate with a polyol containing 20 to 80 parts by weight of a polycaprolactonepolyol and 10 to 60 parts by weight of triglyceride ricinoleate, the ratio of the molar quantity of an isocyanate group in the aromatic polyisocyanate to the molar quantity of a hydroxyl group in the polyol being 1:1 to 1:1.2.

A coated granule obtained by coating a bioactive substance-containing granule with a urethane resin obtained by reacting 20 to 50 parts by weight of an aromatic polyisocyanate with a polyol containing 20 to 80 parts by weight of a polycaprolactonepolyol and 14 to 50 parts by weight of triglyceride ricinoleate, the ratio of the molar quantity of an isocyanate group in the aromatic polyisocyanate to the molar quantity of a hydroxyl group in the polyol being 1:1 to 1:1.2.

A coated granule obtained by coating a bioactive substance-containing granule with a urethane resin obtained by reacting 15 to 60 parts by weight of an aromatic polyisocyanate, 20 to 80 parts by weight of a polycaprolactonepolyol and 10 to 60 parts by weight of the hydroxy fatty acid ester in the presence of a catalyst.

A coated granule obtained by coating a bioactive substance-containing granule with a urethane resin obtained by reacting 20 to 50 parts by weight of an aromatic polyisocyanate, 20 to 80 parts by weight of a polycaprolactonepolyol and 14 to 50 parts by weight of the hydroxy fatty acid ester in the presence of a catalyst.

A coated granule obtained by coating a bioactive substance-containing granule with a urethane resin obtained by reacting 15 to 60 parts by weight of an aromatic polyisocyanate, 20 to 80 parts by weight of a polycaprolactonepolyol and 10 to 60 parts by weight of triglyceride ricinoleate in the presence of a catalyst.

A coated granule obtained by coating a bioactive substance-containing granule with a urethane resin obtained by reacting 20 to 50 parts by weight of an aromatic polyisocyanate, 20 to 80 parts by weight of a polycaprolactonepolyol and 14 to 50 parts by weight of triglyceride ricinoleate in the presence of a catalyst.

The coated granule of the present invention can be produced by forming a coat made of the above-mentioned urethane resin around a bioactive substance-containing granule, and the coating method is not particularly restricted. There are mentioned, for example, (1) a method in which a solution or emulsion of a urethane resin prepared separately is sprayed around a bioactive substance-containing granule, then, a solvent is removed to attain coating; (2) a method in which an aromatic polyisocyanate and a polyol are added simultaneously or sequentially to a bioactive substance-containing granule, and on the surface of the bioactive substance-containing granule, a urethane resin is prepared to attain coating; (3) a method in which a bioactive substance-containing granule is allowed to contain either an aromatic polyisocyanate or a polyol previously, then, another raw material of a urethane resin is reacted, to perform coating on the surface of the bioactive substance-containing granule; and other methods.

Desired elution suppressing ability can be obtained even if the use amount of a resin used for coating is smaller providing a coat film in the coated granule of the present invention is uniform. Thus, it is preferable that the urethane resin is produced by reacting an aromatic polyisocyanate and a polyol under the condition of no solvent on the surface of a granular material containing a bioactive substance.

Examples of the coated granule of the present invention used for applications in the agricultural field include coated granular fertilizers, coated agricultural granular materials, solid agricultural chemical-containing microcapsules, solid agricultural chemical-containing microspheres and the like.

In obtaining the coated granule of the present invention, coating can be performed without using a solvent in resin molding, if an un-hardened urethane resin has suitable flowability for a suitable period at temperatures in producing a urethane resin.

In the coated granule of the present invention, it is preferable that a urethane resin has a hydrophobic liquid compound having a boiling point of 100° C. or higher from the standpoint of bioactive substance elution suppressing ability. The hydrophobic liquid compound is usually immersed in a urethane resin or supported on its surface. The hydrophobic liquid compound is liquid at 20° C., and examples thereof include aliphatic hydrocarbons such as liquid paraffin and the like, aromatic hydrocarbons such as phenylxylylethane, distyrylxylene, Solvesso 150 (trade name: Exxon Mobile Chemical) and the like, petroleum aromatic compounds such as vegetable oils such as soybean oil, cotton seed oil, and the like, and preferable is liquid paraffin.

In the coated granule of the present invention, it is preferable that the above-mentioned hydrophobic liquid compound is contained in an amount of 0.01 to 2 wt % in the coated granular material of the present invention, and in general, it is preferable that the hydrophobic liquid compound is added in an amount to an extent of slight presence of the hydrophobic liquid compound on the surface of the coated granule of the present invention.

The method for producing a coated granule of the present invention will be illustrated in more detail referring to a method for producing a coated granular fertilizer as an example.

Particles of a granular fertilizer are made into fluidizing condition or tumbling condition in an apparatus such as a jet flow apparatus, rolling pan, rolling drum and the like. The size of the particle is not particularly restricted, and usually 0.1 to 15 mm, and its shape is preferably sphere, and may also be other configuration such as cylinder and the like. The particles under fluidizing or tumbling condition are, if necessary, heated. Next, an un-hardened urethane resin as a mixture of an aromatic polyisocyanate, a polyol and, a catalyst to be added if necessary, is added to the particle under fluidizing or tumbling condition. The addition method may be either a method of mixing components before quick addition, or a method of adding components separately. Thereafter, while maintaining the fluidizing or tumbling condition of the particles, the reaction of an isocyanate group in the aromatic polyisocyanate and a hydroxyl group in the polyol is progressed, thereby, the surface of the particle is coated with a urethane resin. It is preferable to control the amount of the urethane resin to be added so that the thickness of a coat film formed in this one operation is usually 1 to 20 μm. Further, when larger thickness of a coat film is necessary, the thickness of a coat film of a urethane resin can be increased by repeating the above-mentioned operation.

In the coated granule of the present invention, the thickness of a coat film of a urethane resin is usually 1 to 600 μm, preferably 8 to 400 μm, and the amount thereof is usually 1 to wt % based on coated granular material of the present invention), preferably 2 to 16 wt % in terms of weight.

The particle size of the coated granule of the present invention is usually in the range of 0.1 to 15 mm.

When a urethane resin has a hydrophobic liquid compound, the coated granular fertilizer of the present invention can be produced by a method in which a hydrophobic liquid compound is added to the granular fertilizer simultaneously with an un-hardened urethane resin, a method in which a hydrophobic liquid compound is added to the granular fertilizer before coating with a urethane resin, a method in which a hydrophobic liquid compound is added, after coating with a urethane resin, to the granular fertilizer coated with a urethane resin, and the like, in the above-mentioned method for producing a coated granular fertilizer, and preferably, produced by a method in which a hydrophobic liquid compound is added to the granular fertilizer before coating with a urethane resin.

EXAMPLES

The present invention will be illustrated in more detailed by production examples and test examples mentioned later, but the present invention is not limited to only examples.

Reference Example

Fabrication of Urethane Resin Film

A urethane resin film was fabricated under the following conditions.

Polyols described in Table 1 and 2,4,6-tris (dimethylaminomethyl)phenol (catalyst) were mixed uniformly at about 50° C., then, an aromatic polyisocyanate was added, and mixed quickly, and drawn into a sheet using an applicator set at a thickness of about 125 μm (for degradation test). The drawn resin was allowed to standstill at 70° C. for 3 hours to cause hardening, obtaining urethane resin films (A) to (G).

TABLE 1

| | Name of compound | A | B | C | D | E | a |
|---|---|---|---|---|---|---|---|
| Poly isocyanate | Polymeric MDI (NCO equivalent: 136) | 20.0 | 25.0 | 30.0 | 25.0 | 25.0 | 25.0 |
| Polyol | Polycaprolactonediol A (hydroxyl equivalent: 265) | | 40.0 | 31.0 | 8.7 | | |
| | Polycaprolactonediol B (hydroxyl equivalent: 492) | 11.3 | 41.0 | 9.0 | 46.3 | 15.9 | 18.1 |
| | Polycaprolactonediol C (hydroxyl equivalent: 1002) | 38.7 | | | | 9.1 | 56.9 |
| | Industrial castor oil (hydroxyl equivalent: 351) | 30.0 | 30.0 | 30.0 | 20.0 | 50.0 | |
| catalyst | 2,4,6-tris(dimethyl aminomethyl)phenol | 0.05 | 0.05 | 0.05 | 0.05 | 0.05 | 0.05 |
| Total amount (wt %) | | 100.05 | 100.05 | 100.05 | 100.05 | 100.05 | 100.05 |
| Average molecular weight of polyol | | 1349 | 965 | 728 | 910 | 1100 | 1603 |

TABLE 2

| | Name of compound | F | G |
|---|---|---|---|
| Polyisocyanate | Polymeric MDI (NCO equivalent: 136) | 30.0 | 30.0 |
| Polyol | Polycaprolactonediol A (hydroxyl equivalent: 265) | 32.0 | 25.0 |
| | Polycaprolactonediol C (hydroxyl equivalent: 1002) | 18.0 | 5.0 |
| | Industrial castor oil (hydroxyl equivalent: 351) | 20.0 | 40.0 |
| catalyst | 2,4,6-tris (dimethylaminomethyl)phenol | 0.05 | 0.05 |
| Total amount (wt %) | | 100.1 | 100.05 |
| Average molecular weight of polyol | | 693 | 768 |

In Tables 1 and 2 described above, polymeric MDI (polymethylene polyphenylene polyisocyanate, Sumidur 44V-10, manufactured by Sumika Beyer Urethane K.K.), polycaprolactonediol A (Placcel 205, manufactured by Daicel Chemical Industries, Ltd.), polycaprolactonediol B (Placcel 210, manufactured by Daicel Chemical Industries, Ltd.), polycaprolactonediol C (Placcel 220, manufactured by Daicel Chemical Industries, Ltd.), polycaprolactonediol D (Placcel 208, manufactured by Daicel Chemical Industries, Ltd.), industrial castor oil (Industrial castor oil No. 1, containing triglyceride ricinoleate as a main component in an amount of about 70 wt %, manufactured by Toyokuni Seiyu K.K.), 2,4,6-tris(dimethylaminomethyl)phenol (TAP, manufactured by Kayaku Akzo Corporation).

Test Example 1

Film Permeability Test of Urethane Resin Film

Using a film permeability experiment apparatus (manufactured by VIDREX, for flat plate film), film permeability of urea in films (A), (B), (C), (D), (E) and film (a) were measured. 53 ml of a 72% aqueous urea solution was charged in one cell of the film permeability experiment apparatus, and 53 ml of ion exchanged water was charged in another cell (acceptor side), and the film was sandwiched between these cells and kept at 50° C. During the test, the solution in each cell was being stirred by a stirrer. After given days, the aqueous solution was sampled from the acceptor side, and the amount of urea permeated through the film was measured. Based on degrees of film permeation calculated by the following calculation formula, relative degrees of film permeation of films of the urethane resin, hypothesizing the degree of film permeation of film (a) is 1, are shown in Table 3.

[degree of film permeation (mol/(hr×m))]=[urea permeation molar quantity per unit area (mol/(hr×m$^2$))]×[film thickness (m)]

TABLE 3

|  | Relative degree of permeation |
|---|---|
| Film (A) | 0.33 |
| Film (B) | 0.20 |
| Film (C) | 0.13 |
| Film (D) | 0.36 |
| Film (E) | 0.08 |

Test Example 2

Degradation of Urethane Resin Film in Soil

Films (F) and (G) were cut into a size of 20×20 mm and buried in soil obtained from the field in Hyogo prefecture (clay loam having a moisture content of 25.9%) and preserved at 28° C. During preservation, moisture was refilled appropriately in the soil and kept constant. Three months after, the films were recovered, washed with water, and dried, then, reduction rate in weight of the film was measured. Film (F) showed a reduction of 6 wt %, and film (G) showed a reduction of 3 wt %.

Production Example 1

Under conditions described later, coated granular fertilizers were produced by coating 1000 parts by weight of granular urea (large granular urea, particle size: about 3 mm, number of granule per g: 60) with 100 parts by weight of urethane resins of raw material compositions (F) and (G) described in Table 3.

In a rotary bath, 1000 parts by weight of granular urea was made into tumbling condition, and the granular urea was heated up to about 70° C. by hot air. Next, 15 parts by weight of liquid paraffin was added and rolling thereof was continued for 10 minutes. Further, while maintaining the tumbling condition, 5 parts by weight of an unhardened urethane resin having the composition described in Table 1 was added. The unhardened urethane resin added was obtained by mixing a polyol described in Table 1 and 2,4,6-tris(dimethylaminomethyl)phenol (catalyst) at about 50° C. uniformly, then, adding an aromatic polyisocyanate directly before addition, and mixing them quickly. After addition of the unhardened urethane resin, the tumbling condition was kept under heating for 3 minutes or more. Further, addition of the unhardened urethane resin and keeping of the tumbling condition under heating for 3 minutes were repeated until the total amount of the unhardened urethane resin added reached 100 parts by weight. Thereafter, the mixture was cooled down to around room temperature, to obtain coated granular ureas (F) and (G).

Test Example 3

Test of Elution Property of Urea in Coated Granular Fertilizer 7.5 g of the coated granular fertilizer obtained in Production Example 1 was placed in a 100 ml glass tube, 100 ml of ion-exchanged water was added to this and the mixture was allowed to stand still at 25° C. After given time, a small amount of the mixture was sampled, and the urea content eluted from the coated fertilizer was measured. As a result, the elution ratio after 7 days was 4% for the coated granular urea (F) and 2% for the coated granular urea (G), meaning sufficient control of initial elution.

Production Example 2

Eight (8) parts by weight of N-(1,1,3-trimethyl-2-oxa-4-indanyl)-5-chloro-1,3-dimethylpyrazole-4-carboxamide, 1.6 parts by weight of hydrous silicon dioxide (TOKUSEAL GU-N, manufactured by Tokuyama Soda Co., Ltd.) and 8 parts by weight of bentonite (BENTONITE FUJI, manufactured by Hojun Kogyo K.K.) were mixed sufficiently, then, pulverized by a jet mill. 17.6 parts by weight of the pulverized material obtained above, 3 parts by weight of polyvinyl alcohol (mixture of 2.5 parts by weight of GOSENOL GL-05 (manufactured by Nippon Synthetic Chemical Industry Co., Ltd.) and 0.5 parts by weight of PVA 217S (manufactured by Kuraray Co., Ltd.)), 12 parts by weight of bentonite (BENTONITE FUJI, manufactured by Hojun Kogyo K.K.), 2 parts by weight of polyoxyethylene styryl phenyl ether (SOLPOL T-20, manufactured by Toho Chemical Industry Co., Ltd.) and 50.4 parts by weight of a calcium carbonate powder (TANCAL NN200, manufactured by Nitto Funka Kogyo K.K.) were mixed sufficiently in a juice mixer, to obtain a powder mixture. To the powder mixture was added 15 parts by weight of water containing 7.5 parts by weight of granulated sugar and 7.5 parts by weight of urea dissolved therein, and the mixture was kneaded sufficiently. The resultant kneaded material was granulated by a compact extrusion granulation machine equipped with a 0.9 mm φ screen, and the particle size was regulated, then, the granules were dried at 60° C. for 15 minutes to obtain an inner core in the form of cylinder (granule size: 1400 to 850 µm, average diameter of cross-section: 0.9 min φ).

In a rotary bath, 100 parts by weight of the above-mentioned inner core was made into tumbling condition, and the inner core was heated up to about 80° C. by hot air. Next, 0.25 parts by weight of an unhardened urethane resin composed of 24.6 wt % of MDI (diphenylmethane diisocyanate, Sumidur 44S, manufactured by Sumika Beyer Urethane K.K.), 40.9 wt % of polycaprolactonediol D (Placcel 208, manufactured by Daicel Chemical Industries, Ltd.), 34.5 wt % of industrial castor oil (molecular weight 920, industrial castor oil No. 1, containing triglyceride ricinoleate as a main component, manufactured by Toyokuni Seiyu K.K.) and 0.05 wt % of 2,4,6-tris(dimethylaminomethyl)phenol (TAP, manufactured by Kayaku Akzo Corporation) was added. The unhardened urethane resin added was obtained by previously mixing a polyol component and 2,4,6-tris(dimethylaminomethyl)phenol (catalyst) at 50° C. uniformly, and adding to this an aromatic polyisocyanate directly before addition, and mixing them quickly. After addition of the unhardened urethane resin, the tumbling condition was kept under heating for 3 minutes or more. Further, addition of the unhardened urethane resin and keeping of the tumbling condition under heating for 3 minutes were repeated until the total amount of the unhardened urethane resin added reached 5.00 parts by weight. Thereafter, the mixture was cooled down to around room temperature, to obtain coated agricultural chemical granule (A).

Test Example 4

Test of Elution Property of Agricultural Chemical Component of Coated Agricultural Chemical Granule Two hundred (200) mg of the coated agricultural chemical granule (A) obtained in Production Example 2 was placed in a 100 ml glass tube, 100 ml of ion-exchanged water was added to this and the mixture was allowed to stand still at 25° C. After given time, a small amount of the mixture was sampled, and the content of N-(1,1,3-trimethyl-2-oxa-4-indanyl)-5-chloro-1,3-dimethylpyrazol-4-carboxamide eluted from the coated fertilizer was measured. As a result, the elution ratio of the coated agricultural chemical granule (A) after one week was 26%.

Production Example 3

Eight (8) parts by weight of N-(1,1,3-trimethyl-2-oxa-4-indanyl)-5-chloro-1,3-dimethylpyrazole-4-carboxamide, 1.6 parts by weight of hydrous silicon dioxide (TOKUSEAL GU-N, manufactured by Tokuyama Soda Co., Ltd.) and 8 parts by weight of bentonite (BENTONITE FUJI, manufactured by Hojun Kogyo K.K.) were mixed sufficiently, then, pulverized by a jet mill. 17.6 parts by weight of the crushed material obtained above, 4.5 parts by weight of a pulverized mixture of 3.15 parts by weight of [(E)-1-(2-chloro-1,3-thiazol-4-ylmethyl)-3-methyl-2-nitroquanidine] and 1.35 parts by weight of clay (SHOKOSAN Clay S, manufactured by Shokosan Kogyosho K.K.), 3 parts by weight of a mixture of 2.5 parts by weight of polyvinyl alcohol (GOSENOL GL-05 (manufactured by Nippon Synthetic Chemical Industry Co., Ltd.) and 0.5 parts by weight of PVA 217S (manufactured by Kuraray Co., Ltd.), 12 parts by weight of bentonite (BENTONITE FUJI, manufactured by Hojun Kogyo K.K.), 2 parts by weight of polyoxyethylene styryl phenyl ether (SOLPOL T-20, manufactured by Toho Chemical Industry Co., Ltd.) and 51.9 parts by weight of a calcium carbonate powder (TANCAL NN200, manufactured by Nitto Funka Kogyo K.K.) were mixed sufficiently in a juice mixer, to obtain a powder mixture. To the powder mixture was added 15 parts by weight of water containing 12.0 parts by weight of granulated sugar and 1.5 parts by weight of urea dissolved therein, and the mixture was kneaded sufficiently. The resultant kneaded material was granulated by a compact extrusion granulation machine equipped with a 0.9 mm φ screen, and the particle size was regulated, then, the granules were dried at 60° C. for 15 minutes to obtain an inner core in the form of cylinder (granule size: 1900 to 850 μm, average diameter of cross-section: 0.9 mm φ).

In a rotary bath, 100 parts by weight of the above-mentioned inner core was made into tumbling condition, and the inner core was heated up to about 70° C. by hot air, then, 0.25 parts by weight of an unhardened urethane resin A was added. The unhardened urethane resin A was obtained by previously mixing 47.7 parts by weight of polycaprolactonepolyol (molecular weight: 832, Placcel 208, manufactured by Daicel Chemical Industries, Ltd.), 21.1 parts by weight of propylene glycol monoricinoleate (molecular weight: 368, manufactured by Ito Seiyu K.K.) and 0.05 parts by weight of 2,4,6-tris(dimethylaminomethyl)phenol (catalyst) uniformly, and adding to this 31.19 parts by weight of polymeric MDI (Sumidur 44V-10, manufactured by Sumika Beyer Urethane K.K.) directly before addition, and mixing them. After addition of the unhardened urethane resin, the tumbling condition was kept under heating for 3 minutes or more. Further, addition of the unhardened urethane resin A and keeping of the tumbling condition under heating for 3 minutes were repeated until the total amount of the unhardened urethane resin added reached 4.00 parts by weight. Thereafter, the mixture was cooled down to around room temperature, to obtain coated agricultural chemical granule (B). The polyols used in this production example had an average molecular weight of 599.

INDUSTRIAL APPLICABILITY

In the coated granule containing a bioactive substance, a resin forming a coat shows degradability in soil, and there is controllability of suitable elution of the bioactive substance.

The invention claimed is:
1. A coated granule obtained by coating a bioactive substance-containing granule with a urethane resin obtained by reaction of an aromatic polyisocyanate with a polyol having an average molecular weight of 300 to 5000, wherein the polyol contains a polycaprolactonepolyol and a hydroxy fatty acid ester of the formula (I):

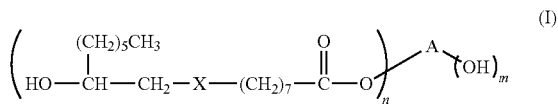

(wherein, X represents —CH$_2$—CH$_2$- or —CH=CH—, n represents 1, 2 or 3, m represents 0, 1 or 2, and n+m is 2 or 3. In the case of n+m=2, A represents a C$_2$ to C$_8$ alkanediyl group, and in the case of n+m=3, A represents a C$_3$ to C$_8$ alkanetriyl group.).

2. The coated granule according to claim 1, wherein the total content of a polycaprolactonepolyol and a hydroxy fatty acid ester of the formula (I) in the polyol is 50 wt % or more.

3. The coated granule according to claim 1, which is obtained by coating a bioactive substance-containing granule with a urethane resin obtained by reaction of an aromatic polyisocyanate with a polyol having an average molecular weight of 300 to 5000, wherein the polyol contains a polycaprolactonepolyol and at least one selected from castor oil and hydrogenated castor oil.

4. The coated granule according to claim 3, wherein the total content of a polycaprolactonepolyol and at least one selected from castor oil and hydrogenated castor oil in the polyol is 70 wt % or more.

5. The coated granule according to claim 1, wherein the amount of the polycaprolactonepolyol is 20 to 80 parts by weight based on 100 parts by weight of the total amount of the aromatic polyisocyanate and polyol.

6. The coated granule according to claim 1, wherein the amount of the hydroxy fatty acid ester of the formula (I) is 10 to 60 parts by weight based on 100 parts by weight of the total amount of the aromatic polyisocyanate and polyol.

7. The coated granule according to claim 1, wherein the amount of the aromatic polyisocyanate is 15 to 60 parts by weight based on 100 parts by weight of the total amount of the aromatic polyisocyanate and polyol.

8. The coated granule according to claim 1, wherein the total amount of the aromatic polyisocyanate, polycaprolactonepolyol and hydroxy fatty acid ester of the formula (I) is 70 to 100 parts by weight based on 100 parts by weight of the total amount of the aromatic polyisocyanate and polyol.

9. The coated granule according claim 1, wherein the hydroxy fatty acid ester of the formula (I) is triglyceride ricinoleate.

10. The coated granule according to claim 1, wherein the aromatic polyisocyanate is polymethylenepolyphenyl polyisocyanate.

11. The coated granule according to claim 1, wherein the bioactive substance is a fertilizer.

12. The coated granule according to claim 1, wherein the bioactive substance is a pesticide.

* * * * *